(12) United States Patent
Parins et al.

(10) Patent No.: US 6,293,945 B1
(45) Date of Patent: Sep. 25, 2001

(54) ELECTROSURGICAL INSTRUMENT WITH SUCTION CAPABILITY

(75) Inventors: David J. Parins, Corcoran; Scott T. Latterell, Minneapolis, both of MN (US)

(73) Assignee: Everest Medical Corporation, Minneapolis, MN (US)

( * ) Notice: Subject to any disclaimer, the term of this patent is extended or adjusted under 35 U.S.C. 154(b) by 0 days.

(21) Appl. No.: 09/518,943

(22) Filed: Mar. 6, 2000

(51) Int. Cl.[7] ................................................. A61B 18/18
(52) U.S. Cl. ................................... 606/45; 606/48; 606/49
(58) Field of Search ........................... 606/41, 42, 45–51; 604/35

(56) References Cited

U.S. PATENT DOCUMENTS

| | | | |
|---|---|---|---|
| 4,116,198 | * | 9/1978 | Roos ........................................ 606/46 |
| 4,919,129 | | 4/1990 | Weber, Jr. et al. . |
| 5,085,657 | | 2/1992 | Ben-Simhon . |
| 5,197,963 | * | 3/1993 | Parins ...................................... 606/46 |
| 5,318,565 | * | 6/1994 | Kuriloff et al. ......................... 606/49 |
| 5,360,427 | | 11/1994 | Majlessi . |
| 5,395,312 | * | 3/1995 | Desai ....................................... 604/22 |
| 5,401,274 | * | 3/1995 | Kusunoki ................................ 606/41 |
| 5,449,356 | | 9/1995 | Walbrink et al. . |
| 5,735,849 | * | 4/1998 | Baden et al. ............................ 606/51 |
| 5,895,386 | * | 4/1999 | Odell et al. ............................. 606/50 |
| 5,913,857 | * | 6/1999 | Ritchart et al. ......................... 606/45 |
| 5,968,042 | | 10/1999 | Ernster . |
| 5,989,249 | * | 11/1999 | Kirwan, Jr. ............................. 606/50 |

\* cited by examiner

*Primary Examiner*—Michael Peffley
(74) *Attorney, Agent, or Firm*—Nikolai & Mersereau, P.A.

(57) ABSTRACT

A surgical instrument for performing three functions at the tip of a tube. The first function is for suction or irrigation of an area where surgery is being performed. The tubing can have a vacuum attached for sucking solid particles, liquids, gases or smoke from the area adjacent the end of the tubing. The tubing may also be used to pump fluids into the area adjacent the end of the tube to flush the area or apply a treatment. The tubing has an electrical current such that when the tube is applied to blood it will coagulate the blood. The tubing also has a cutting electrode for electrically cutting tissue. The cutting electrode extends out from the lumen of the tube and retracts therein when not in use. Therefore a surgeon has three instruments compactly arranged at his disposal at the distal end of the tube. Since the tube can be made long and thin it is useful when operating in a limited space and can be used in laparascopic or other microsurgeries. The tube is malleable for shaping it for ease of use. Thus the surgeon can electrically cut, suck out blood, smoke and other debris and electrically coagulate blood all with one instrument and at preferred angles or shapes.

22 Claims, 3 Drawing Sheets

ELECTROSURGICAL INSTRUMENT WITH SUCTION CAPABILITY

BACKGROUND OF THE INVENTION

1. Field of the Invention

This invention relates to electrosurgical devices for cutting and coagulation combined with suction and irrigation capability.

2. Description of the Related Art

In the past there have been electrosurgical devices which have been used for coagulation combined with suction. There have also been electrosurgical devices for cutting combined with suction. These devices may also provide fluids for irrigating the area being operated on by pumping fluids through the tubes normally used for suction.

It would be useful to have one tool for both electrical cutting and electrical coagulation while providing suction, the device having a small cross section for laparascopic or other microsurgery.

There have been no known devices that have combined electrosurgical cutting and coagulation with the suction so as to have both the cutting with suction and coagulation with suction in one tool.

SUMMARY OF THE INVENTION

The invention combines a retractable electrosurgical cutting electrode with an electrosurgical coagulation electrode and a suction or irrigation tube. A surgeon may now use one device having a small cross section for cutting, coagulating, mechanical disecting, irrigating and suction.

The device has a tube with an insulating sleeve, the tip of which is exposed for electrical coagulation. The tube lumen is used for aspiration and/or delivering fluids for irrigation or medication. Two aspiration suctions are available, a low vacuum for removing smoke and a higher vacuum for removing blood and other debris.

An electrical blade is extended from the lumen of the tube for cutting and dissection, and retracted into the lumen of the tube at other times. When the electrical cutting blade is retracted, the tip of the tube can be used for coagulation. Thus repeated cutting and coagulation steps are possible by extending and retracting the electrical blade.

The tube is preferably malleable and may have the cutting electrode extend from inside the lumen of the tube or from adjacent the tube. Alternatively, the tube may be extendable, moving over a stationary cutting electrode.

A thumb slide may be used in the movable blade embodiment to extend or retract the cutting blade. Likewise, in an alternative embodiment the thumb slide moves the tube such that the blade is either exposed or covered. The thumb slide engages detents which provide a tactile response and locks into a position indicating exposure or covering of the blade, thus reducing errors.

OBJECTS OF THE INVENTION

It is an object of the invention to provide a multifunctional electrosurgical instrument having a cutting electrode for cutting at desired times.

It is an object of the invention to provide a coagulation electrode and means for aspirating and/or irrigating the surgical site obviating the need for instrument exchanges to accomplish such functions.

It is an object of the invention to extend or retract the cutting electrode for use or at the end of an electrosurgical coagulation electrode.

It is an object of an alternative embodiment of the invention to extend or retract the tube over the cutting electrode.

It is an object of the invention to combine the suction tube, the coagulation tube electrode and the cutting electrode in one tube for compactness so as to permit open procedures, laparascopic surgery or microsurgery.

It is an object of the invention to provide a flexible tube for desired shaping to the required use.

It is an object of the invention to provide a low suction vacuum for removing smoke and a higher suction vacuum for removing debris.

Other objects, advantages and novel features of the present invention will become apparent from the following detailed description of the invention when considered in conjunction with the accompanying drawing.

DESCRIPTION OF THE PREFERRED EMBODIMENTS

Figure 1:
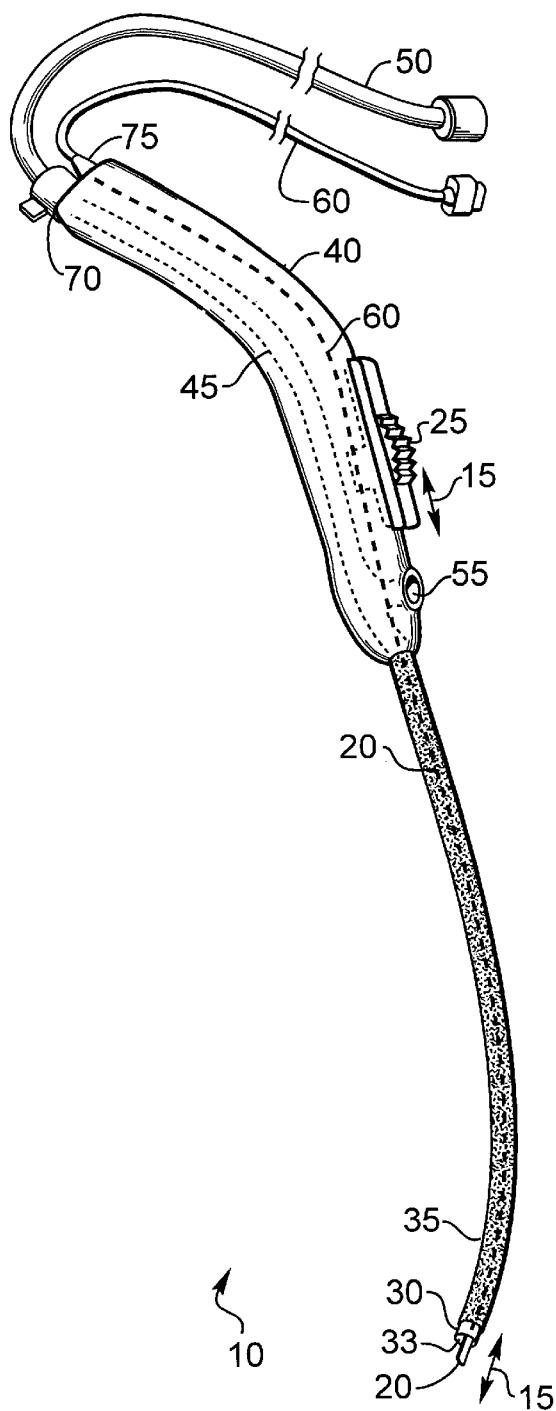
FIG. 1 is a perspective view of a first embodiment of the electrosurgical instrument.
Figure 2:
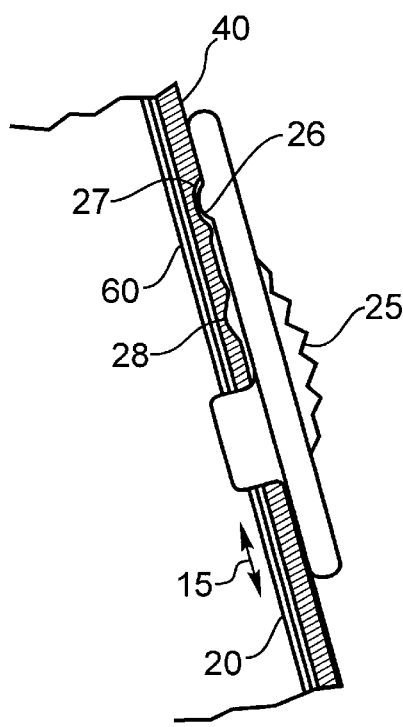
FIG. 2 is a cross sectional view of the thumb slide.

The electrosurgical instrument 10 shown in FIG. 1 has an extensible and retractable electrosurgical cutting electrode 20 which is extended or retracted in directions 15 by thumb slide 25. When it is desired to use the electrosurgical cutting electrode 20 for cutting, the thumb slide 25 extends the electrosurgical cutting electrode 20 out from inside of the lumen 33 of metal tube 30. The electrosurgical cutting electrode 20 is in electrical contact with metal tube 30 to receive a monopolar RF voltage for surgical cutting, as is well known in the art. The patient is typically grounded by a grounding pad to complete the electrical circuit.

The metal tube 30 is surrounded by an insulating sleeve 35, which covers all but a predetermined portion of the distal tip of metal tube 30. The exposed portion of the metal tube 30 is used to electrically coagulate blood during surgery when the tip of the metal tube 30 is in contact with the area to be coagulated. Although the metal tube 30 is shown with a circular portion exposed, a semicircular portion or other portion may be exposed to limit the portion of the distal tip which will cauterize for a better controlled more accurate application of cauterization of the surgical work area.

The lumen 33 of the metal tube 30 is used as a suction path for a vacuum to remove solid particles, liquids or gasses from the area being operated on. The lumen 33 of the metal tube 30 may also be used for irrigating an area being operated on by pumping fluids therethrough.

Figure 3:
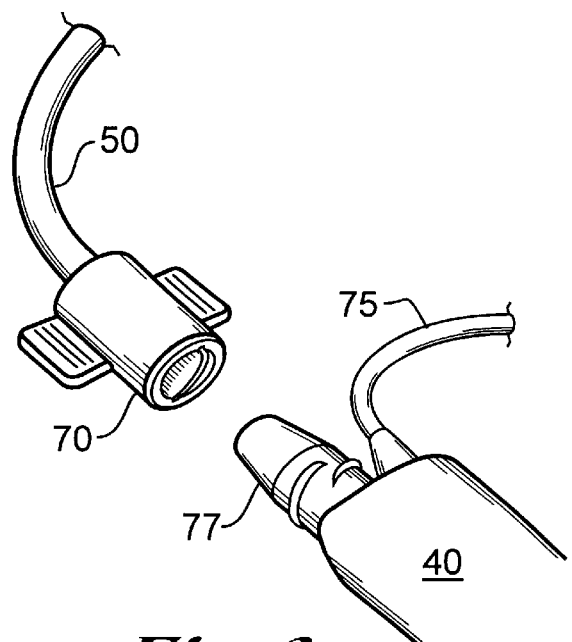
FIG. 3 is a perspective view of the suction tube coupling on the handle.

The metal tube 30 and the insulating sleeve 35 extend from a lumen 45 in handle 40. The handle lumen 45 is connected to a tube 50 by coupling 77 (see FIG. 3) for connection to a vacuum for suction, or to a fluid supply for flushing the area operated on. The tube 50 is fluidly connected to the metal tube 30 inside the handle 40 via a lumen 45 which is preferably molded into the handle 40. The proximal end of the handle 40 has a coupling 77 to attach to the attachment point 70 on tube 50. The lumen 45 of the handle 40 contains a suction aperture 55 fluidly connected to the tube 50. When a constant suction is applied through tube 50 the suction aperture 55 allows the surgeon the option of having a high suction or a low suction at the distal tip of the metal tube 30. The high suction is obtained when the surgeon covers the aperture 55 with his thumb or finger. The low suction is obtained when aperture 55 is uncovered allowing a portion of the vacuum to escape. A high suction is typically used to remove debris while a low suction is used to remove smoke during application of RF energy.

Electrical lead 60 is in electrical contact with and provides a source of power to the metal tube 30 and therethrough to cutting electrode 20. The electrical lead 60 passes through the handle 40 to the metal tube 30. There is an attachment point 75 at the proximal end of the handle 40 to secure the electrical lead 60 so that it does not become dislodged from the connection to the metal tube 30.

The metal tube 30 is a long thin tube such that it can be used in open procedures, laparascopic or microsurgery. The metal tube 30 is preferably malleable so that it can be bent into any desired shape for ease of use. The metal tube 30 provides three functions: first, it is a fluid conduit for providing suction or a flushing fluid to the area being operated on; second it provides an electric current for coagulating the area being operated on at the distal tip of the metal tubing 30; third it provides a sheath for retractable cutting electrode 20 so that it can be deployed only when needed for cutting or mechanical dissection.

Preferably the cutting electrode 20 extends a variable length from the tip of the metal tube 30. In some embodiments the cutting electrode 20 extends to a maximum of about 1 centimeter from the tip of the metal tube 30. The extension of the cutting electrode 20 is controlled by thumb slide 25. The thumb slide 25 has an extension 26 which extends into indent 27 in the handle 25 to indicate that the cutting electrode 20 is safely positioned inside of the metal tube 30. When moving the thumb slide 25 forward, the extension 26 thereon is removed from indent 27 and is pushed forward until it rests in indent 28 indicating the cutting electrode 20 is fully extended. The surgeon therefore knows the cutting electrode 20 is fully retracted and will not affect the patient when the thumb slide extension 26 clicks into position at detent 27, and is fully extended for cutting when the thumb slide 25 clicks into position at detent 28. Since the indents 27 and 28 require some force to overcome, the cutting electrode 20 is not likely to be accidentally extended or retracted.

Figure 4:
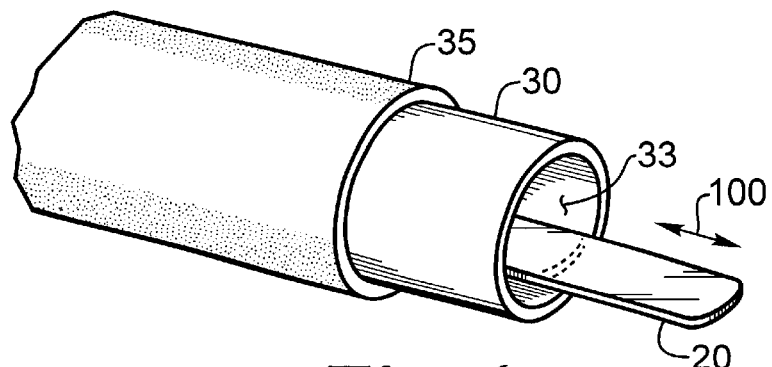
FIG. 4 is a perspective of the extendable cutting blade inside the tube.
Figure 5:
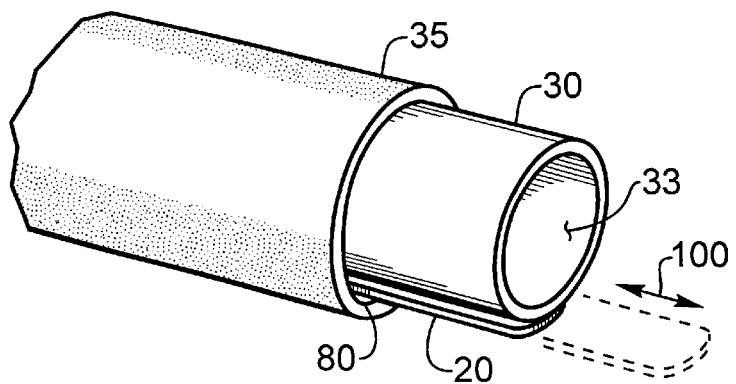
FIG. 5 is a perspective of the extendable cutting blade outside the tube.

In the first embodiment as shown in FIGS. 1 and 4, the cutting electrode 20 is inside the lumen 33 of tube 30. As FIG. 4 shows, the cutting electrode is extended as shown by arrow 100 to the exposed and projected position. In an alternate embodiment shown in FIG. 5, the cutting electrode 20 lies outside of the tube 30 and in a lumen 80 between the insulating sleeve 35 and the tube 30. Cutting electrode 20 is extended and retracted by thumb slide 25, as in the embodiment shown by FIG. 4, and moves as shown by arrows 100.

Figure 6:
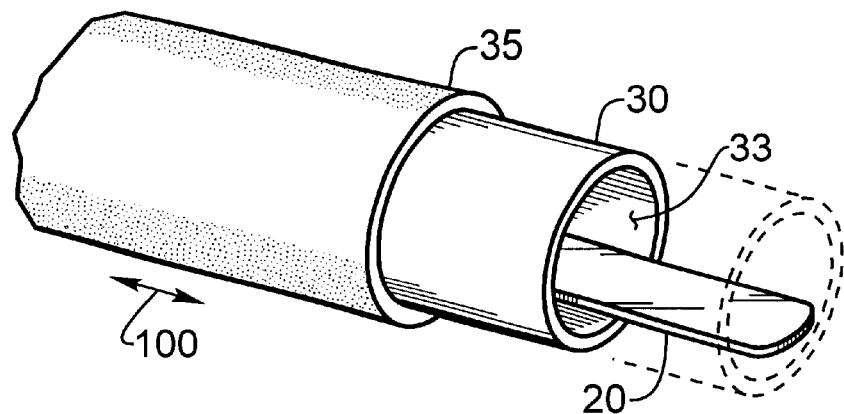
FIG. 6 is a perspective of the extendable tube with the cutting blade inside the tube.

In a further embodiment, shown in FIG. 6, the tube 30 is slidably attached to the handle 40 and extends or retracts to positions as shown by arrows 100 by moving thumb slide 25 as before. When the tube 30 is retracted partly into housing 40 the fixed cutting electrode 20, which is inside tube 30, is exposed to enable cutting and mechanocal dissection. When the tube 30 is extended, it covers cutting electrode 20. The exposed tip of the tube 30, having no insulation 35, is used to coagulate the area being operated on.

Figure 7:
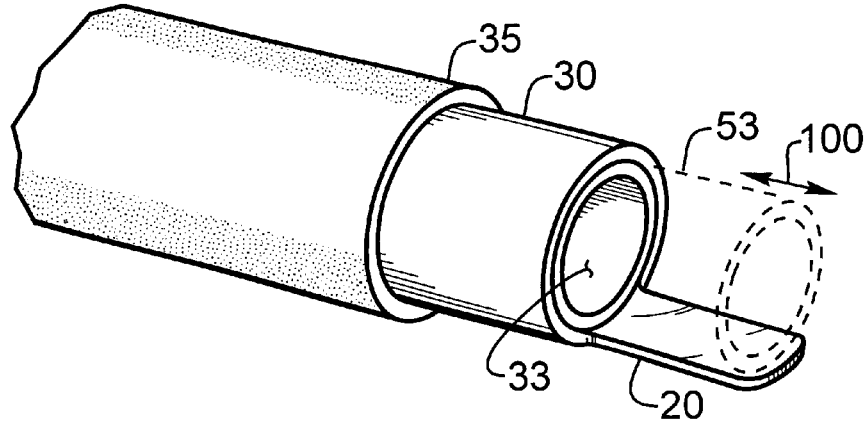
FIG. 7 is a perspective of the extendable tube with the cutting blade outside the tube.

In FIG. 7 the cutting electrode 20 is fixed as an extension at the end of tube 30 and insert tube 53 inside of tube 30 extends and retracts as shown by arrows 100 to cover and uncover cutting electrode 20 as thumb slide 25 is extended and retracted. The insert tube 53 is extended for use in coagulation.

Figure 8:
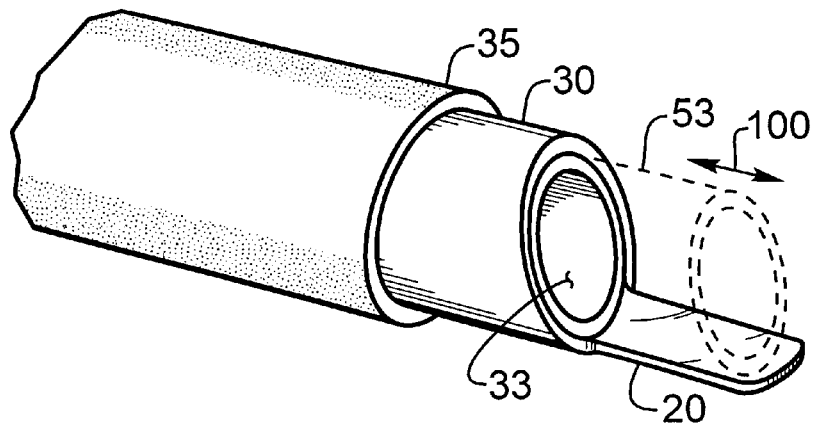
FIG. 8 is a perspective of the extendable tube angled and the cutting blade outside the tube.

FIG. 8 shows an embodiment similar to that shown by FIG. 7, except that the end of the insert tube is angled for ease of use in some applications.

The electrosurgical instrument 10 can be used in surgery with the operating area in view, or inserted into the body during laparascopic surgery. The surgeon can mechanically dissect electrically cut, electrically coagulate blood, and remove blood, smoke and other debris, and irrigate, all with one instrument.

In an alternative embodiment the metal tube 30 may be a malleable tube, which need not be a conductor, such that isolative material 35 would not be needed. The tip of the malleable tube may have a ring or portion of a ring made of a conductive material in electrical contact with an RF power source for providing power to coagulate the area being operated on.

Obviously, many modifications and variations of the present invention are possible in light of the above teachings. It is therefore to be understood that, within the scope of the appended claims, the invention may be practiced otherwise than as specifically described.

What is claimed is:

1. An electrosurgical instrument comprising:

a handle, having a lumen therethrough for transporting fluids, a tube, having a lumen, extending distally from the handle, and fluidly connected to the lumen in the handle, an exposed electrode at the distal tip of the tube, an electrical lead in electrical contact with the electrode, for supplying electrical power thereto, a connection for a proximal tube to be fluidly connected to the lumen of the handle and the tube for supplying a vacuum thereto such that a suction can be supplied at the distal tip of the tube and for supplying a flushing fluid at the distal tip of the tube, a cutting electrode in electrical contact with the electrode for cutting when the cutting electrode is brought into contact with a target tissue, a means for covering and exposing the cutting electrode such that the cutting electrode can be exposed when it is desired to cut the target tissue and covered when the cutting electrode is not to cut tissue.

2. An electrosurgical instrument as in claim 1 wherein:

a suction aperture, fluidly connected to the lumen in the handle such that a portion of the suction is diverted through the suction aperture when it is left uncovered thereby reducing the suction applied at the distal tip of the electricity conducting metal tubing.

3. An electrosurgical instrument as in claim 2 wherein:

the means for covering and exposing the cutting electrode comprises an extendable cutting electrode residing in a lumen adjacent the outside of the tube, the lumen having the cutting electrode therein being electrically insulated to prevent electrical contact.

4. An electrosurgical instrument as in claim 3 wherein:

a thumb slide slidably attached to the handle and connected to the cutting electrode for extending and retracting the cutting electrode in and out of the lumen such that when extended the cutting electrode is exposed for cutting.

5. An electrosurgical instrument as in claim 4 wherein:

the thumb slide has an extension, and the handle has a first indentation and a second indentation, such that the extension on the thumb slide extends into the first indentation on the handle when the cutting electrode is in the covered position and the thumb slide extension extends into the second indentation on the handle when the cutting electrode is in the exposed position.

6. An electrosurgical instrument as in claim 2 wherein:

the means for covering and exposing the cutting electrode comprises a fixed position cutting electrode in slidable electrical contact with the electrode, inside the lumen of the tube, the tube being an extendable tube, moving relative the handle and the cutting electrode, such that the extendable tube in a first position exposes the cutting electrode for use and in a second position covers the cutting electrode.

7. An electrosurgical instrument as in claim 6 wherein:

a thumb slide slidably attached to the handle and connected to the extendable tube for extending and retracting the extentable tube.

8. An electrosurgical instrument as in claim 7 wherein:

the thumb slide has an extension and the handle has a first indentation and a second indentation such that the extension on the thumb slide extends into the first indentation on the handle when the cutting electrode is in the covered position and the thumb slide extension extends into the second indentation on the handle when the cutting electrode is in the uncovered position.

9. An electrosurgical instrument as in claim 2 wherein:

the means for covering and exposing the cutting electrode comprises a fixed position cutting electrode on the end of the tube, a covering tube inside the lumen of the tube and extendable relative to the tube, the handle and the cutting electrode, such that the covering tube in a first position exposes the cutting electrode for use and the second tube in a second position covers the cutting electrode.

10. An electrosurgical instrument as in claim 9 wherein:

a thumb slide slidably attached to the handle and connected to the covering tube for extending and retracting the covering tube in and out of the lumen of the tube such that when retracted the cutting electrode is exposed for cutting.

11. An electrosurgical instrument as in claim 10 wherein:

the thumb slide has an extension and the handle has a first indentation and a second indentation such that the extension on the thumb slide extends into the first indentation on the handle when the cutting electrode is in the covered position and the thumb slide extension extends into the second indentation on the handle when the cutting electrode is in the exposed position.

12. An electrosurgical instrument as in claim 2 wherein:

the means for covering and uncovering the cutting electrode includes a thumb slide slidably attached to the handle such that moving the thumb slide to a first position exposes the cutting electrode for use and moving the thumb slide to a second position covers the cutting electrode.

13. An electrosurgical instrument as in claim 12 wherein:

the tube is malleable such that it can be bent it to a desired shape for use.

14. An electrosurgical instrument as in claim 9 wherein:

the covering tube and the tube have angled ends for easy of use.

15. An electrosurgical instrument as in claim 2 wherein:

the tube is an electrically conducting metal tube having, an insulating sleeve covering the electrically conducting metal tube over a substantial portion of the electrically conducting metal tube's length, the insulating sleeve extending from the handle distally and leaving the distal tip of the electrically conducting metal tube uncovered, to form the exposed electrode at the distal tip of the tube, an electrical lead extending through the handle and in electrical contact with the electrically conducting metal tube, for supplying electrical power thereto, and the cutting electrode in electrical contact with the lumen of the electrically conducting metal tube.

16. An electrosurgical instrument as in claim 1 wherein:

the means for exposing and covering the cutting electrode comprises an extendable cutting electrode inside the lumen of the tube.

17. An electrosurgical instrument as in claim 16 wherein:

a thumb slide slidably attached to the handle and connected to the cutting electrode for extending and retracting the cutting electrode in and out of the lumen of the tube such that when extended the cutting electrode is exposed for cutting the target tissue.

18. An electrosurgical instrument as in claim 17 wherein:

the thumb slide has an extension and the handle has a first indentation and a second indentation such that the extension on the thumb slide extends into the first indentation on the handle when the cutting electrode is in the covered position and the thumb slide extension extends into the second indentation on the handle when the cutting electrode is in the exposed position.

19. An electrosurgical instrument as in claim 18 wherein:

the tube is malleable such that it can be bent to a desired shape for use.

20. An electrosurgical instrument as in claim 18 wherein:

the suction aperture is adjacent the thumb slide on the top of the handle.

21. An electrosurgical instrument as in claim 1 wherein:

the electrode is a ring around the tube at the distal tip.

22. An electrosurgical instrument as in claim 1 wherein:

the electrode is a portion of a ring around the tube at the distal tip.

* * * * *